US00PP21736P3

(12) United States Plant Patent
Patel

(10) Patent No.: US PP21,736 P3
(45) Date of Patent: Mar. 1, 2011

(54) BLUEBERRY VARIETY NAMED 'BLUE MOON'

(50) Latin Name: *Vaccinium corymbosum*
Varietal Denomination: Blue Moon

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/590,255

(22) Filed: Nov. 5, 2009

(65) Prior Publication Data

US 2010/0138965 P1 Jun. 3, 2010

Related U.S. Application Data

(60) Provisional application No. 61/198,467, filed on Nov. 6, 2008.

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Greenlee Sullivan PC

(57) ABSTRACT

A new and distinct Northern Highbush blueberry variety is described. The variety results from selection among a population of seedlings derived from crossing the blueberry variety known as 'Nui' (U.S. Plant Pat. No. 6,699) and an unnamed seedling selection called B7.8.1 (not patented). The fruit of this new variety is large, with an attractive appearance characterised by good bloom and good firmness; fruit has an outstanding fruit quality with sweet and aromatic flavour. Mature plant is upright while the young plant is semi-upright with medium to good vigour. The new variety has been named 'Blue Moon'.

9 Drawing Sheets

Genus and species of plant named: *Vaccinium corymbosum.*

Variety denomination: Blue Moon.

BACKGROUND OF THE INVENTION

This new Northern Highbush blueberry variety was selected from a population of seedlings derived from crossing the blueberry varieties known as 'Nui' (seed parent) (U.S. Plant Pat. No. 6,699) and an unnamed seedling selection called B7.8.1 (not patented). The cross was made in 1988 and the new variety was selected in 1996 from among plants located on land at Ruakura, Hamilton, New Zealand, and was assigned the breeder code, RH34. The new variety has since been named 'Blue Moon'.

SUMMARY OF THE INVENTION

The fruit of this new variety is large, with an attractive appearance characterised by good bloom and good firmness; fruit has an outstanding fruit quality with sweet and aromatic flavour. Mature plant is upright while the young plant is semi-upright with medium to good vigour. The new variety was originally referred to as 'RH34' but has since been named 'Blue Moon'.

The new variety is characterised as follows:

Maturity period: Early-mid season, from early December to the end of the month at Ruakura, Hamilton, New Zealand.

Plant form and vigour: The mature plant is upright while the young plant is semi-upright with medium to good vigour, similar to 'Nui'.

Yield: Medium to low, similar to 'Nui'.

Berry size and shape: Big fruit with a characteristic pentagonal shape.

Color: Medium to light blue.

Fruit bloom: Good intensity; attractive.

Pedicel scar: Medium dry scar.

Plant health: The plant has shown symptoms of the early stage of rust infection (*Pucciniastrum vaccinii*) but no subsequent sporulation has been found.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

DETAILED DESCRIPTION

Figure 1:
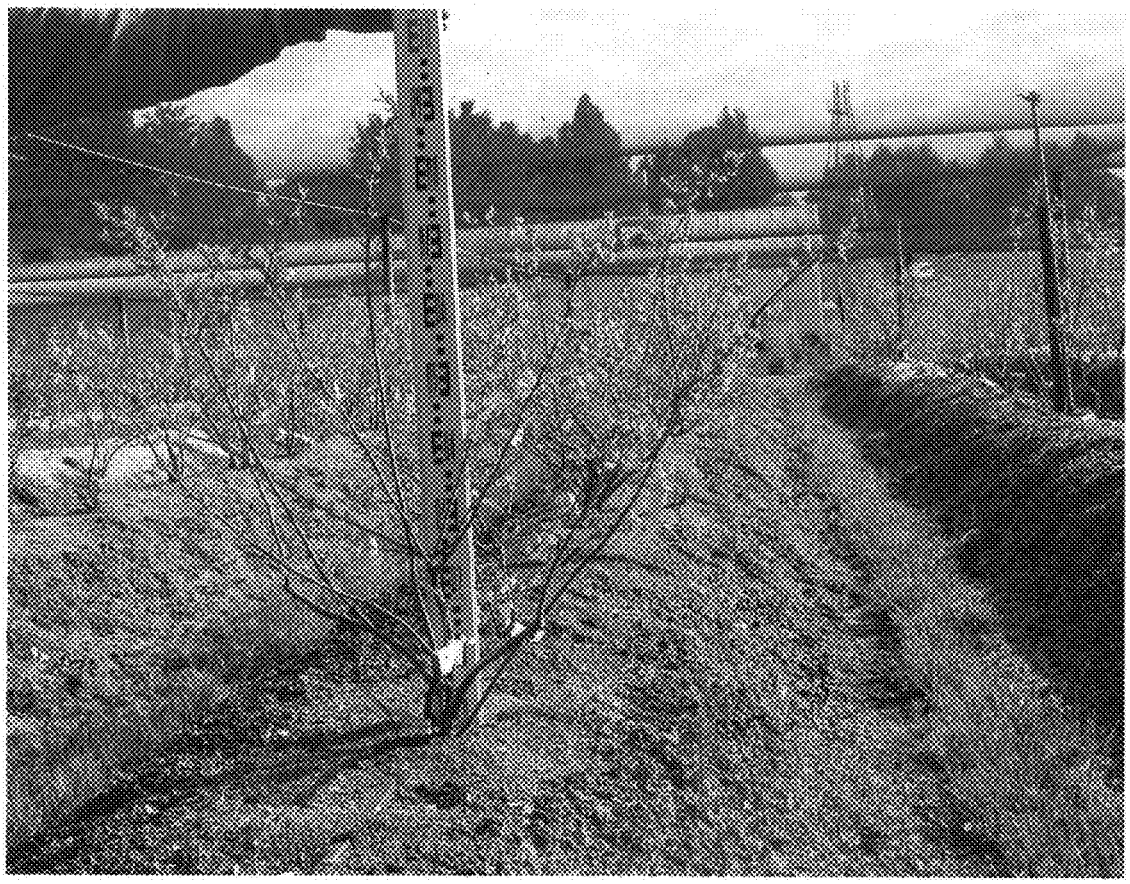
FIG. 1 shows the typical open bush of a young plant of 'Blue Moon'.
Figure 2:
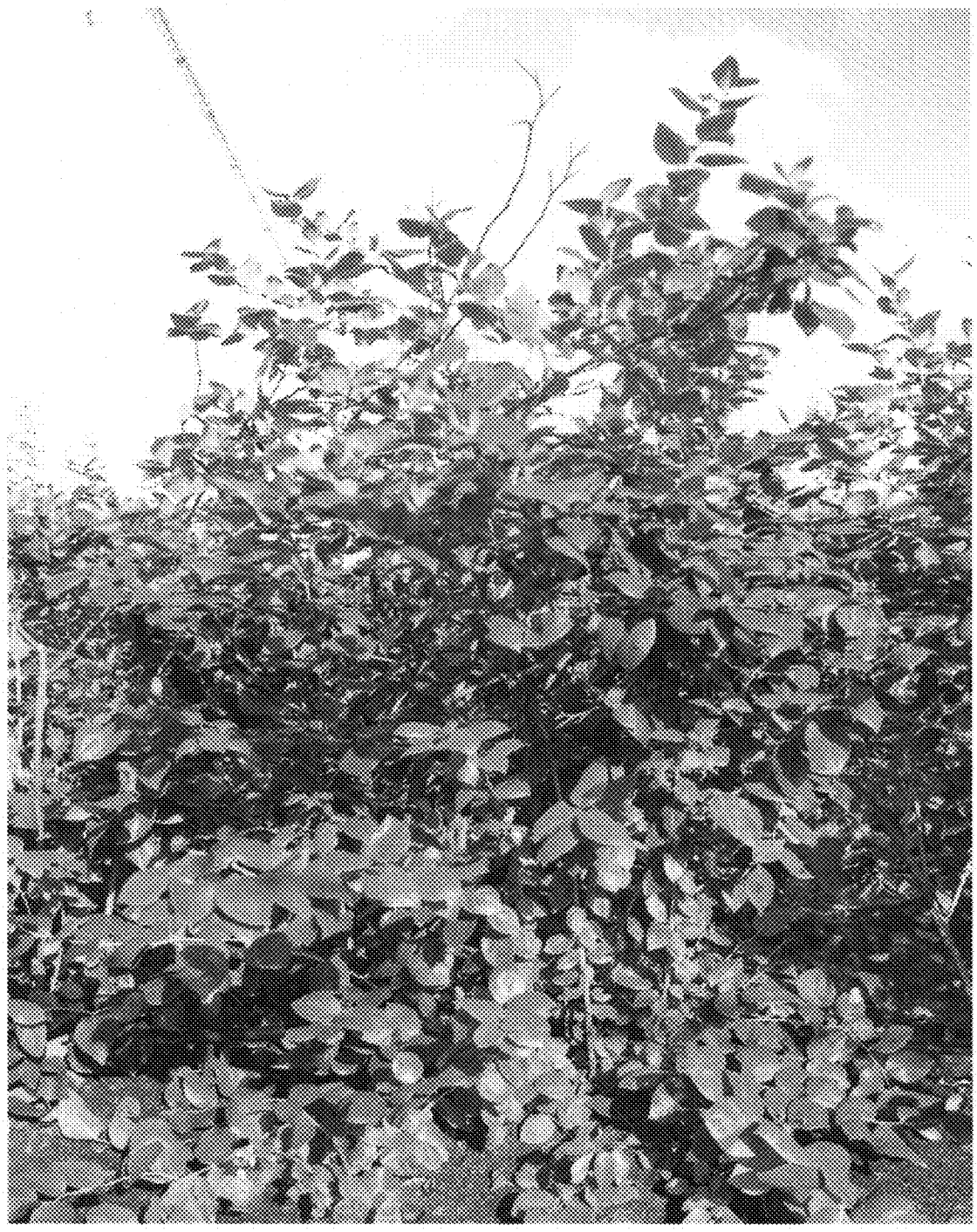
FIG. 2 shows typical adult plants of 'Blue Moon' planted in the field.
Figure 3:
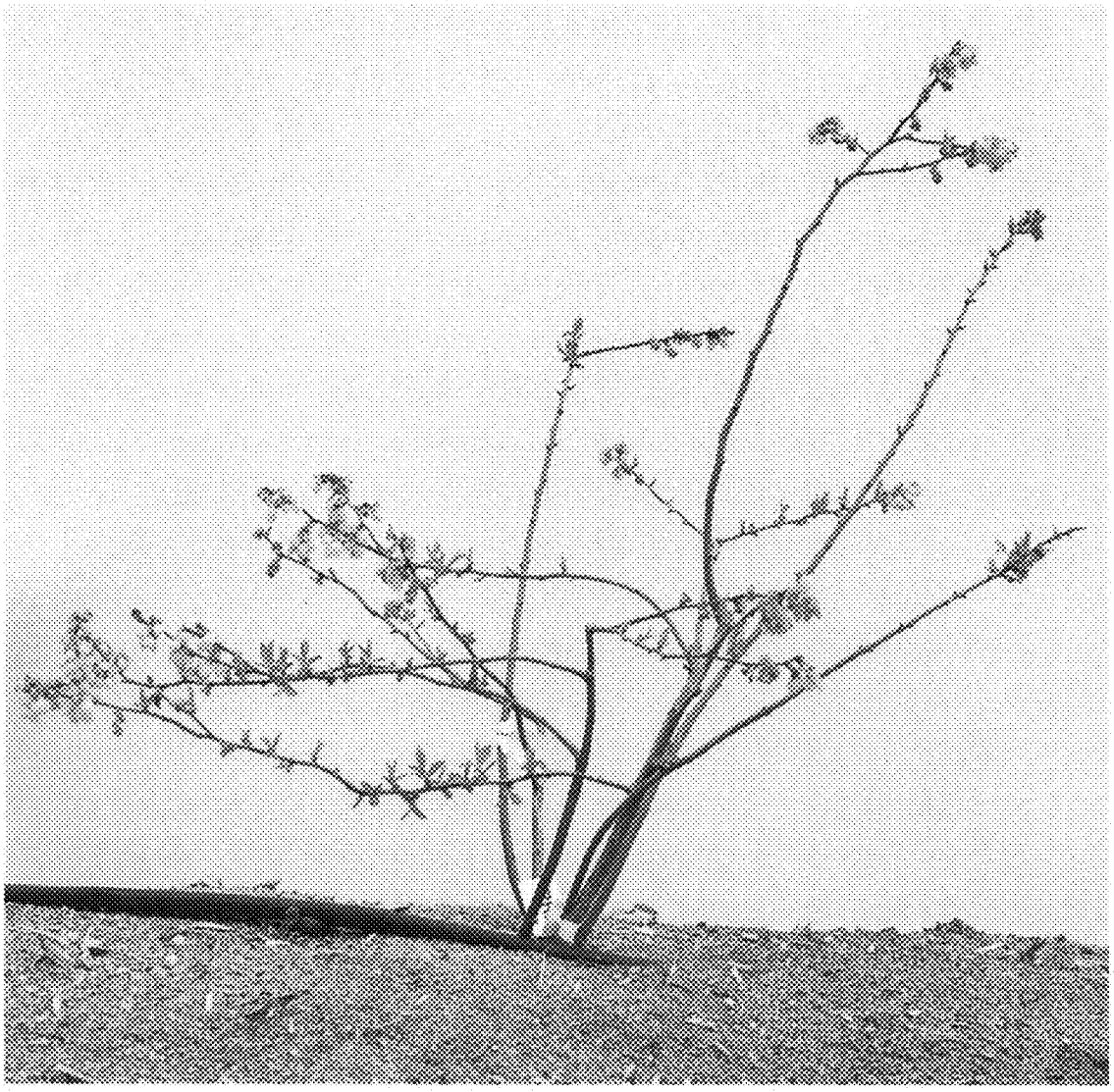
FIG. 3 shows a young plant of 'Blue Moon' during flowering taken in September 2008.
Figure 4:
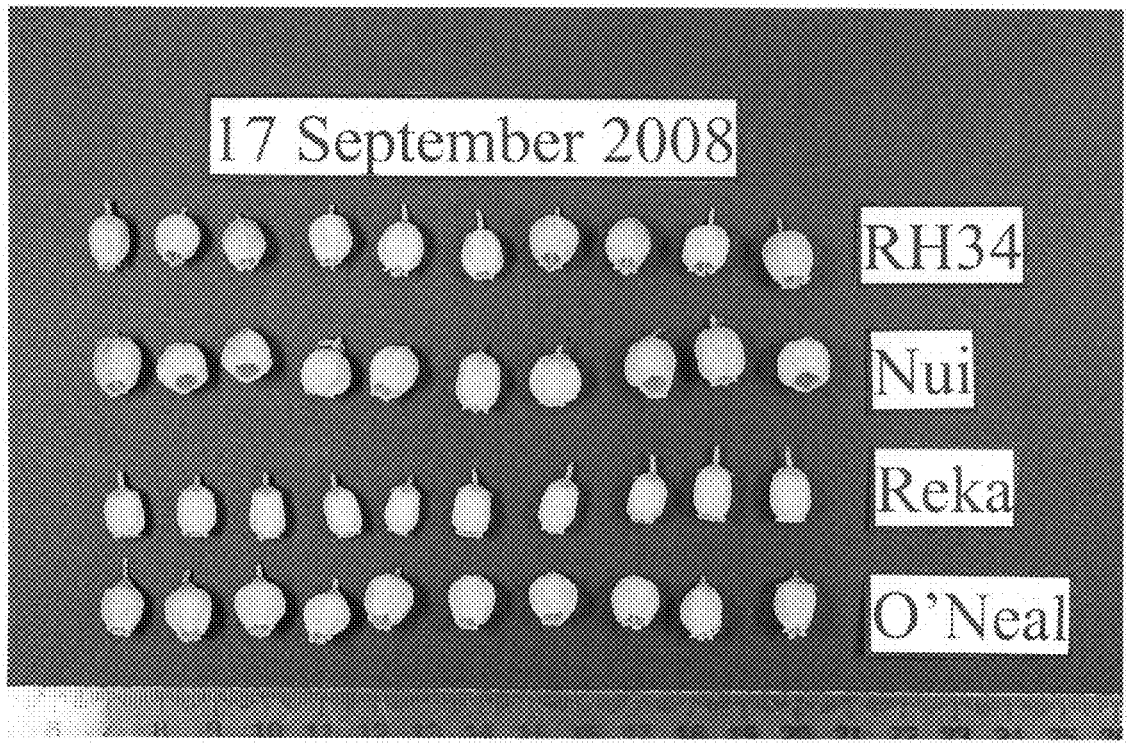
FIG. 4 shows the characteristic flower of 'Blue Moon' (labeled in the figure as 'RH34') compared to flowers of commercial varieties.
Figure 5:
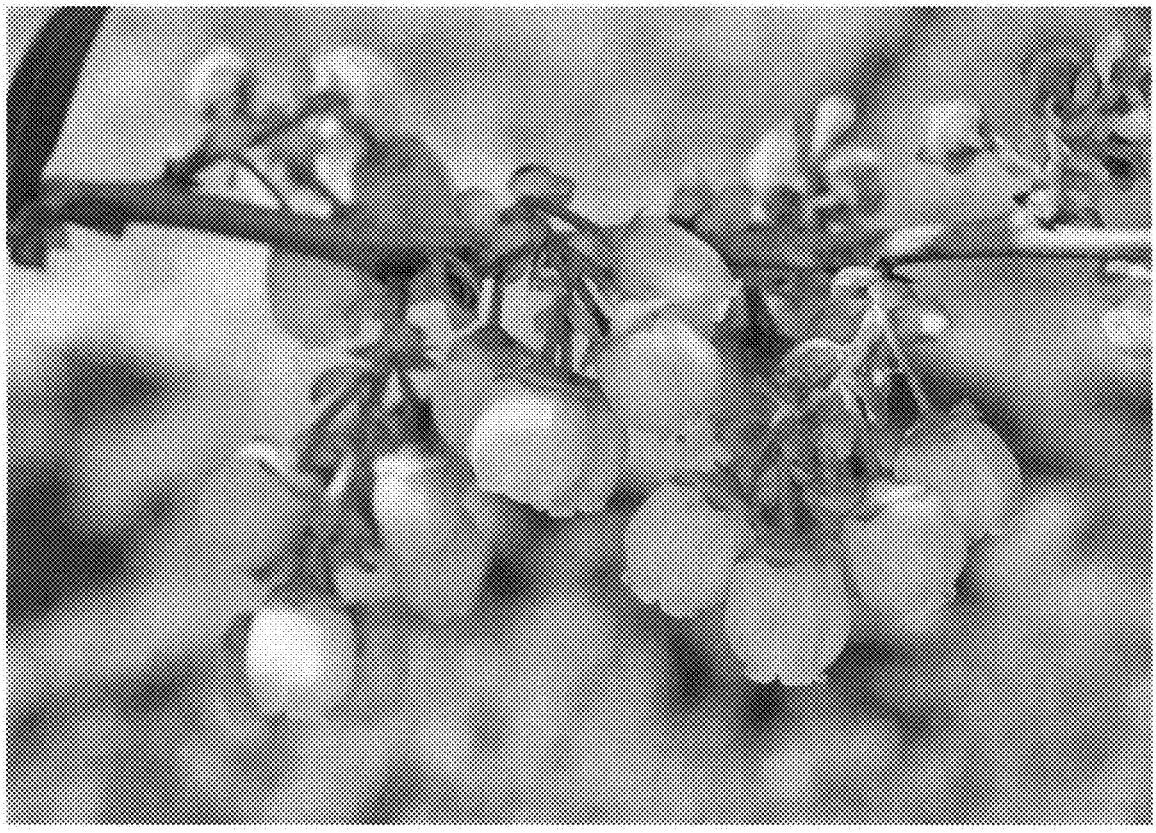
FIG. 5 shows the close up of flower of 'Blue Moon' when fully open.
Figure 6:
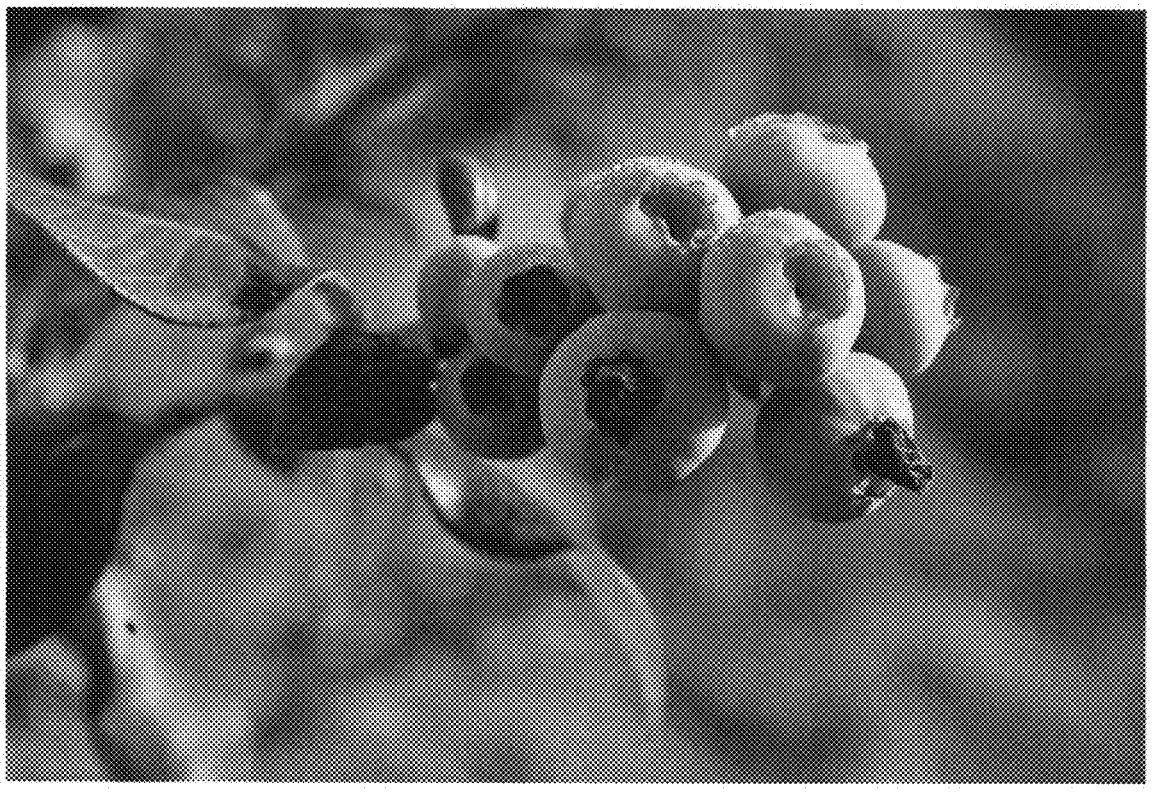
FIG. 6 shows the green fruit of 'Blue Moon'.
Figure 7:
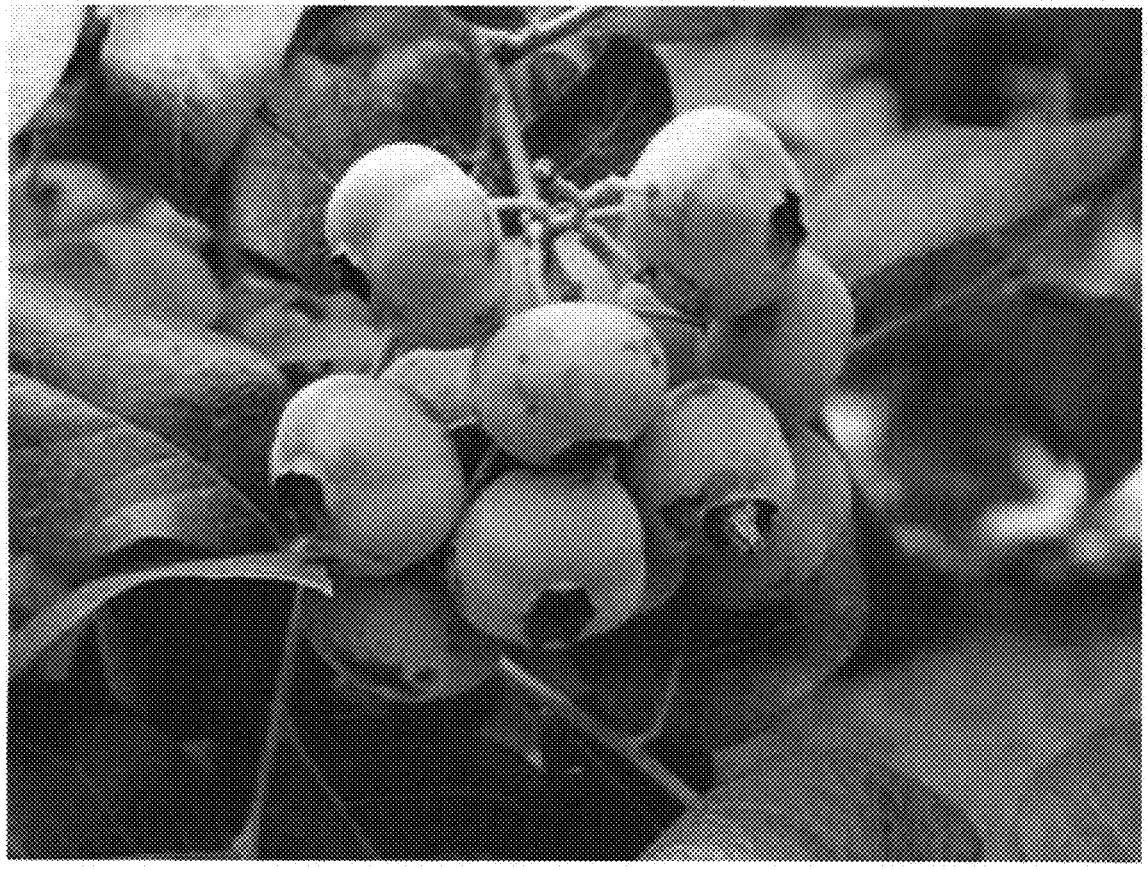
FIG. 7 shows the characteristic fruit cluster of 'Blue Moon'.
Figure 8:
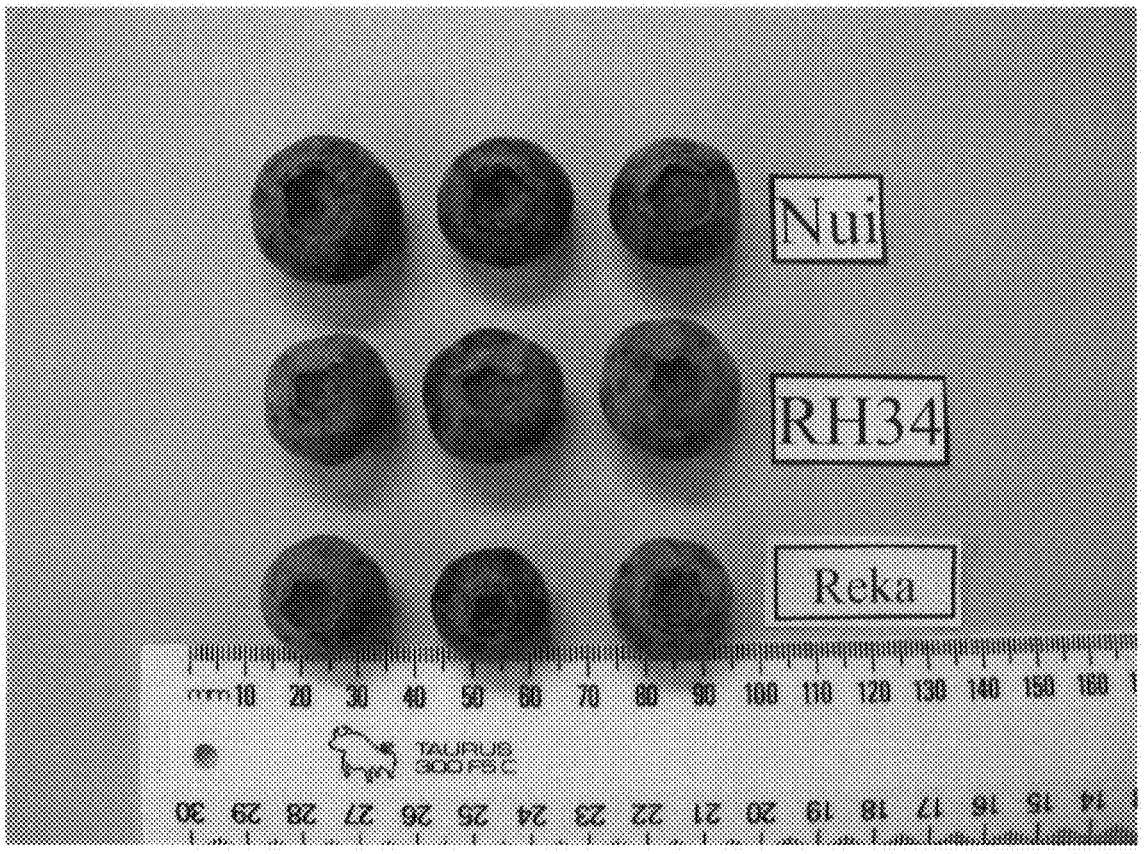
FIG. 8 shows the characteristic big fruit size of 'Blue Moon' (labeled in the figure as 'RH34') compared to the fruit of commercial varieties.
Figure 9A:
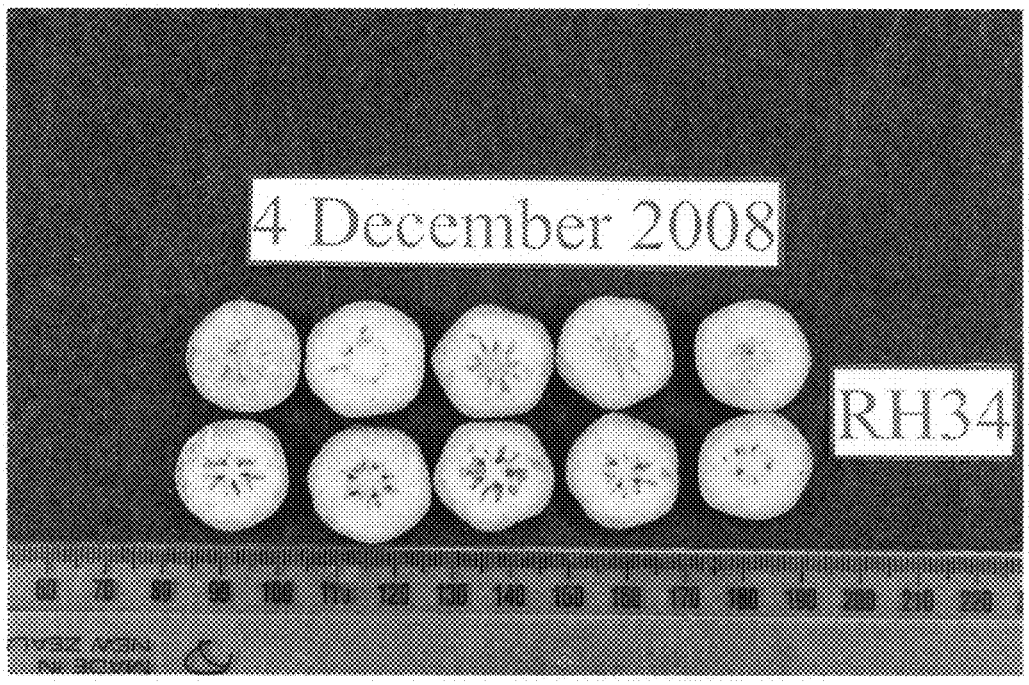
FIGS. 9A and 9B show the fruit sections of 'Blue Moon' (labeled in the figures as 'RH34').
Figure 9B:
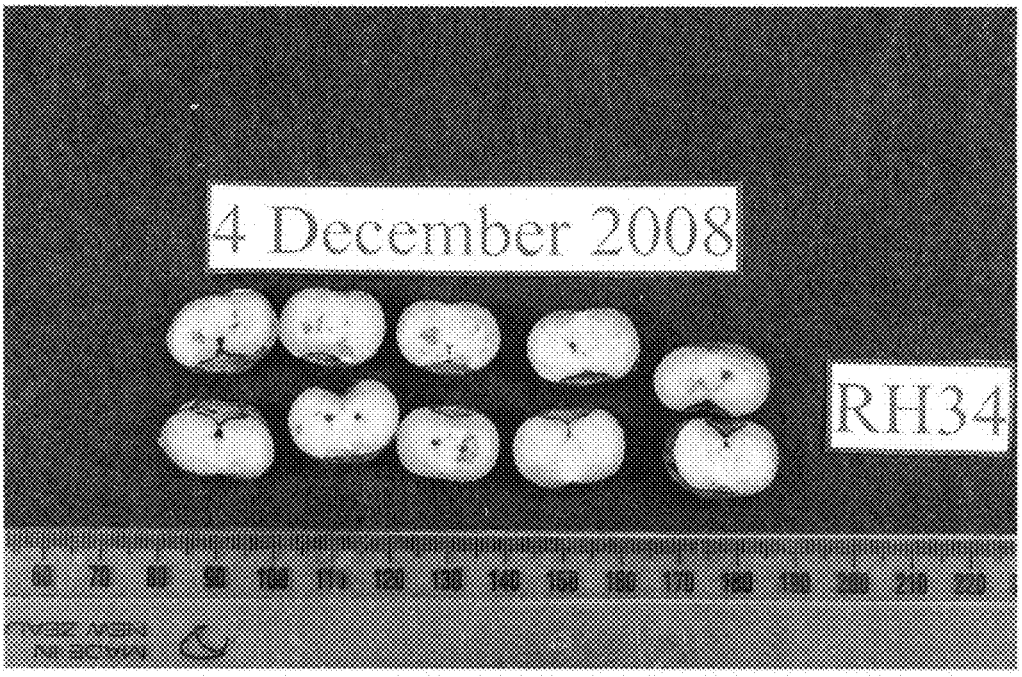

The observations, unless otherwise specified, were made in the 2008 and 2009 seasons on nine year old plants propagated and grown at Ruakura, Hamilton, New Zealand and additional information was collected from young plants (3-5 years old). All dimensions in millimeters, weights in grams (unless otherwise stated). Color terminology is in accordance with The Royal Horticultural Society Colour Charts 2001 edition.

Plant and Foliage

The mature tetraploid plant is upright, with medium to good vigour, similar to 'Nui' while the young plant is semi-upright.

The mature leaf is ovate in shape and typically averages 65 mm in length and approximately 41 mm in width, similar to the leaf size of plants of the variety 'Reka' (U.S. Plant Pat. No. 6,700) (63 mm in length and 36 mm in width) and smaller than those of 'Nui' (80 mm in length, 50 mm in width). Generally the leaf margin has no serration, medium glossiness on the upper surface similar to 'Reka', and no glaucescence on the upper surface. Typically the petiole length averages 4 mm.

The color of the leaf is near Green 137A, differing from those of varieties 'Nui' (near green 146A) and 'Reka' (near green 139A). Leaf vein color is near Yellow-Green 153A, differing from those of the parent variety 'Nui' (near Yellow-Green 152C).

The color of mature dormant wood is near Greyed-Purple 185A and C on the top side of the cane and Yellow-Green 145A and C on the underside of the same cane, differing from that of the parent 'Nui' (near Greyed-Red 181A and B on the top side of the cane and Yellow-Green 146 C on the underside of the same cane).

Inflorescence

The average number of flower buds per shoot is 6, with an observed range of 2-8. The estimation of number of buds per shoot was made on the fruiting (terminal) sections of shoots; this section typically averaging 9 cm in length and the average shoot length is 21 cm.

Flowers are generally clustered and the width of the typical flower averages 9 mm, smaller than 'Nui'. The background color of the petals on fully open mature flowers is near White 155C with anthocyanin coloration ranging near Red-Purple 62B and 62D.

Fruit

The fruit are large to very large under New Zealand growing conditions, averaging approximately 2.7 g. Observations indicate fruit size to be smaller than that of fruit of the parent 'Nui' (3.2 g). Generally, fruit is flat with a characteristic pentagonal shape. Fruit diameter averages approximately 19 mm (observed range 17.6-21.2 mm) under New Zealand growing conditions.

Unripe fruit is green, within the range near Yellow-Green 149B. Ripe fruit has an attractive bloom. Fruit color is light blue with the bloom intact, near Blue group 102B, and skin color when bloom is completely removed is near Black 202A.

The pedicel scar is medium in size, approximately 2 mm in diameter, and is generally dry. The fruit sweetness is medium to strong and the Brix level averages 13%, (observed range 12-15.9%), higher than 'Reka' and 'Nui' (12% and 11.8% respectively).

The fruit acidity measured as titratable acidity (%) averaged 0.6, similar to 'Reka' and less than 'Nui' (0.8%). Fruit is generally firm, averaging 230 g/mm (observed range 180-320 g/mm), firmer compared with fruit of the varieties 'Reka' (averaged 168 g/mm) and 'Nui' (averaged 150 g/mm).

Yield is medium to low, generally around 2 Kg per adult plant, similar to 'Nui' under New Zealand growing conditions.

Seed size is approximately 1.72 mm, with an average number of seeds per fruit of 14 (observed range approximately 5-28).

Events

According to our observations the time of vegetative bud burst was around the 11 September, similar to 'Reka' and about one week later than 'Nui'. Time of beginning flowering recorded in New Zealand was around the same time of the vegetative bud break, reaching an estimated 50% of the flowering around the 3 October, about one week later than 'Nui' and 'Reka'.

The fruit maturity period occurs early to mid season, typically the fruit commenced ripening around the beginning of December to the end of the month at Ruakura, Hamilton, New Zealand. In 2008 the stage where 50% of the fruit were mature was estimated at the 5 December, similar to 'Reka' and about 10 days earlier than 'Nui'.

Disease and Pests

The plant has shown symptoms of the early stage of rust infection (*Pucciniastrum vaccinii*) but no or occasionally very little subsequent sporulation has been observed under New Zealand growing conditions.

Geographical Adaptation

Observations indicate that the variety performs well in the cool temperate climates of the Waikato region, New Zealand, under standard management practices for commercial blueberry production. The plant cold hardiness according to the American zone classification has not been determined.

The invention claimed is:

1. A new and distinct Northern Highbush blueberry variety substantially as described in the specification and illustrations.

* * * * *